United States Patent [19]
Clementi

[11] Patent Number: 5,329,351
[45] Date of Patent: Jul. 12, 1994

[54] PARTICLE DETECTION SYSTEM WITH COINCIDENT DETECTION

[75] Inventor: Lee D. Clementi, Lake Wylie, S.C.

[73] Assignee: Estek Corporation, Charlotte, N.C.

[21] Appl. No.: 980,684

[22] Filed: Nov. 24, 1992

[51] Int. Cl.[5] ............................................. G01N 21/88
[52] U.S. Cl. ................................... 356/237; 250/208.2
[58] Field of Search ........................... 356/237, 446; 250/208.2

[56] References Cited

U.S. PATENT DOCUMENTS

| | | | |
|---|---|---|---|
| 4,197,011 | 4/1980 | Hudson | 356/354 |
| 4,376,583 | 3/1983 | Alford et al. | 356/237 |
| 4,423,331 | 12/1983 | Koizumi et al. | 356/446 |
| 4,464,050 | 8/1984 | Kato et al. | 356/237 |
| 4,556,903 | 12/1985 | Blitchington et al. | 356/237 |
| 4,586,786 | 5/1986 | Suzuki et al. | |
| 4,630,276 | 12/1986 | Moran | 372/15 |
| 4,643,569 | 2/1987 | Sullivan et al. | 356/237 |
| 4,720,191 | 1/1988 | Siegel et al. | 356/237 |
| 4,740,708 | 4/1988 | Batchelder | 356/237 |
| 4,861,164 | 8/1989 | West | 356/445 |
| 4,893,932 | 1/1990 | Kollenberg | 356/369 |
| 5,076,692 | 12/1991 | Neukermans et al. | 356/538 |
| 5,127,726 | 7/1992 | Moran | 356/237 |

FOREIGN PATENT DOCUMENTS

| | | |
|---|---|---|
| 0259036 | 3/1988 | European Pat. Off. |
| 60-69539 | 4/1985 | Japan |
| 2076962 | 12/1981 | United Kingdom |

*Primary Examiner*—Richard A. Rosenberger
*Attorney, Agent, or Firm*—Bell, Seltzer, Park & Gibson

[57] ABSTRACT

The particle detection system detects particles or flaws on the surface of an article. The system has a source of light directed against the surface of the article and a detector for detecting light scattered from the article and indicative of the presence of particles or flaws present on the article. The detector includes a light collector positioned for receiving and collecting light scattered from the surface of the article, a light splitter cooperating with the collector for dividing the collected light into first and second light collect components, first and second photodetectors positioned for receiving respectively first and second like light components, and an electrical circuit for combining the output signals from the first and second photodetectors to form a combined output signal with a higher signal-to-noise ratio than traditional systems.

25 Claims, 2 Drawing Sheets 5,329,351

PARTICLE DETECTION SYSTEM WITH COINCIDENT DETECTION

FIELD OF THE INVENTION

This invention relates to automatic surface inspection systems, and more particularly to the inspection of the surface of an article for detecting flaws or defects in the surface.

BACKGROUND OF THE INVENTION

In the process of manufacturing silicon or other semiconductor microchips, light is generally directed through a reticle mask to etch circuits into a silicon wafer. The presence of dirt, dust, smudges or other foreign matter on the surfaces of the reticle mask or the silicon wafer is highly undesirable and adversely affects the resulting circuits. As a result, the reticles and silicon wafers are necessarily inspected before use. One common inspection technique is for a human inspector to visually examine each surface under intense light and magnification. Debris that is smaller than can be visually detected, however, impairs the resulting microchips.

Laser inspection systems have been developed for inspecting the surface of silicon wafers to accurately detect small particles. Examples of such systems may be seen in U.S. Pat. No. 4,197,011 by Hudson entitled "*Defect Detection And Plotting System*"; U.S. Pat. No. 4,376,583 by Alford et al. entitled "*Surface Inspection Scanning System*"; U.S. Pat. No. 4,630,276 by Moran et al. entitled "*Compact Laser Scanning System*"; U.S. Patent; U.S. Pat. No. 4,643,569 by Sullivan entitled "*Dual Beam Laser Inspection*"; U.S. Pat. No. 4,875,780 by Moran, et al. entitled "*Method and Apparatus For Inspecting Reticles*"; U.S. Pat. No. 5,076,692 by Neukermans, et al. entitled "*Particle Detection On A Patterned Or Bare Wafer Surface*"; U.S. Pat. No. 5,127,726 by Moran entitled "*Method And Apparatus for Low Angle High Resolution Surface Inspection*"; and Japanese Patent 69,539 by Mochizuki entitled "*Inspecting Device For Surface Defect.*"

In these traditional laser inspection systems, light is specularly reflected and scattered from a surface of an article. The specularly reflected and scattered light are both indicative of the presence of particles or flaws on the surface of the article. The light scattered from the reflective surface of the article, such as a silicon wafer disk, is relayed to a single photodetector such as a photomultiplier tube ("PMT"). In the traditional systems, the scattered light consists of a slowly varying base line signal sometimes referred to as haze. The signal typically also contains fast pulses of light which correspond to point defects, such as dust particles on the wafer. The photodetector responds to the base line signal with a direct current ("DC") level offset which is proportional to the haze level. Due to the statistical nature of electron amplification through the diode stages of the PMT, multifrequency alternating current ("AC") noise is generated. This AC noise is random in nature, or asynchronous, and limits capability to distinguish the desired particle signal from this "random" system noise.

Several laser inspection systems have been developed which recognize that the signals detected by various photodetectors do not provide clear indications of fine particles or flaws on the surface of the article. Examples of these systems may be seen in U.S. Pat. No. 4,464,050 by Kato et al. entitled "*Apparatus for Detecting Optically Defects*"; U.S. Pat. No. 4,861,164 by West entitled "*Apparatus for Separating Specular From Diffuse Radiation*"; and U.S. Pat. No. 4,893,932 by Knollenberg entitled "*Surface Analysis And Method.*"These systems, however, failed to reduce the haze level so that detecting the signal from the haze is still difficult.

Thus, there is a need for a laser inspection system which increases signal-to-noise ratio ("S/N") from the scattered light channel detecting particles or flaws, in the surface of an article, such as a silicon wafer.

SUMMARY OF THE INVENTION

The present invention provides a particle detection system having an increased signal-to-noise ratio in the scattered light channel of a laser scanning system.

More particularly, this system has a source of light directed against the surface of the article and a detector for detecting light scattered from the article and indicative of the presence of particles or flaws present on the article. The detector has a light collector positioned for receiving and collecting light scattered from the surface of the article. A light splitter cooperates with the collector to divide the collected light into first and second like light components. First and second photodetectors are positioned for receiving respectively the first and second light components. An electrical circuit is provided for combining the output signals from the first and second photodetectors to form a combined output signal with a higher signal-to-noise ratio than traditional systems.

DESCRIPTION OF THE DRAWINGS

Some of the features and advantages of the present invention having been stated, others will become apparent as the description proceeds when taken in conjunction with the accompanying drawings, in which.

DETAILED DESCRIPTION OF THE ILLUSTRATED EMBODIMENTS

The present invention now will be described more fully hereinafter with reference to the accompanying drawings in which a preferred embodiment of the invention is shown. This invention may, however, be embodied in many different forms and should not be construed as limited to the embodiment set forth herein; rather, this embodiment is provided so that this disclosure will be thorough and complete, and will fully convey the scope of the invention to those skilled in the art. Like numbers refer to like elements throughout.

Figure 1:
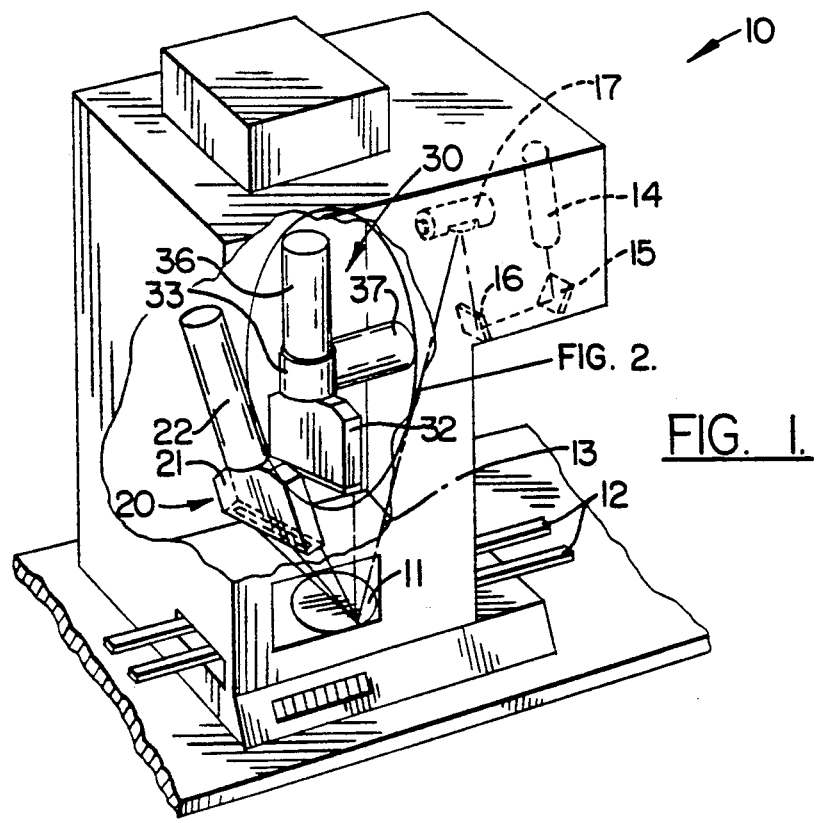
FIG. 1 is a perspective view of a particle detection system according to the present invention with parts broken away for clarity of illustration.

Referring now to the drawings, FIG. 1 is a perspective view of the particle detection system, broadly designated at 10 according to the present invention with parts broken away for clarity. An article, such as a semiconductor wafer 11, is transported along transport means shown as the wafer carrying racks 12. The semiconductor material of the wafer 11 is typically silicon, but it will be apparent to those skilled in the art that the semiconductor material could be of numerous types. The semiconductor wafer 11 is transported along a predetermined path of travel past an inspection zone where a laser beam 13 is scanned along a predetermined path, typically a scan line, in the inspection zone for passing across the surface of the wafer 11. The laser beam 13 is produced from a laser 14, directed to and reflected off a series of mirrors 15, 16, and scanned along the scan line in the inspection zone for passing across the surface of the wafer 11 using a scanning mirror such as the resonant scanner designated at 17.

Also as shown in FIG. 1, light is specularly reflected from the wafer 11 into a light channel detector 20 for detecting particles and non-scattering features on the wafer 11. The light channel detector 20 has a fiber optic bundle 21 positioned to cooperate with a photodetector shown as a photomultiplier tube ("PMT") 22. In addition, light from the laser 14 is scattered from the surface of the wafer 11 to a dark channel detector 30 for detecting light scattered from the semiconductor wafer 11 and indicative of the presence of particles or flaws present on the semiconductor wafer 11. The dark channel detector includes a light collector shown in the form of the fiber optic bundle 32 is positioned for receiving and collecting the light scattered from the surface of the semiconductor wafer 11 along the scan line of the laser beam 13 (discussed further below with reference to FIG. 2). A collar 33 is connected to and adjacent an end of the fiber optic bundle 32 and has a light beam splitter 34 (not shown in FIG. 1) positioned therein. The light beam splitter 34 cooperates with the fiber optic bundle 32 for dividing or splitting the collected light into first and second like light components. The first and second photodetectors shown as photomultiplier tubes 36, 37 are positioned for receiving respectively the first and second like light components. Further, means shown in the form of electrical circuitry 40 in FIG. 2 combine the output signals from the first and second photodetectors 36, 37 to form a combined output signal having a higher signal-to-noise ratio ("S/N") than traditional laser inspection systems.

Figure 2:
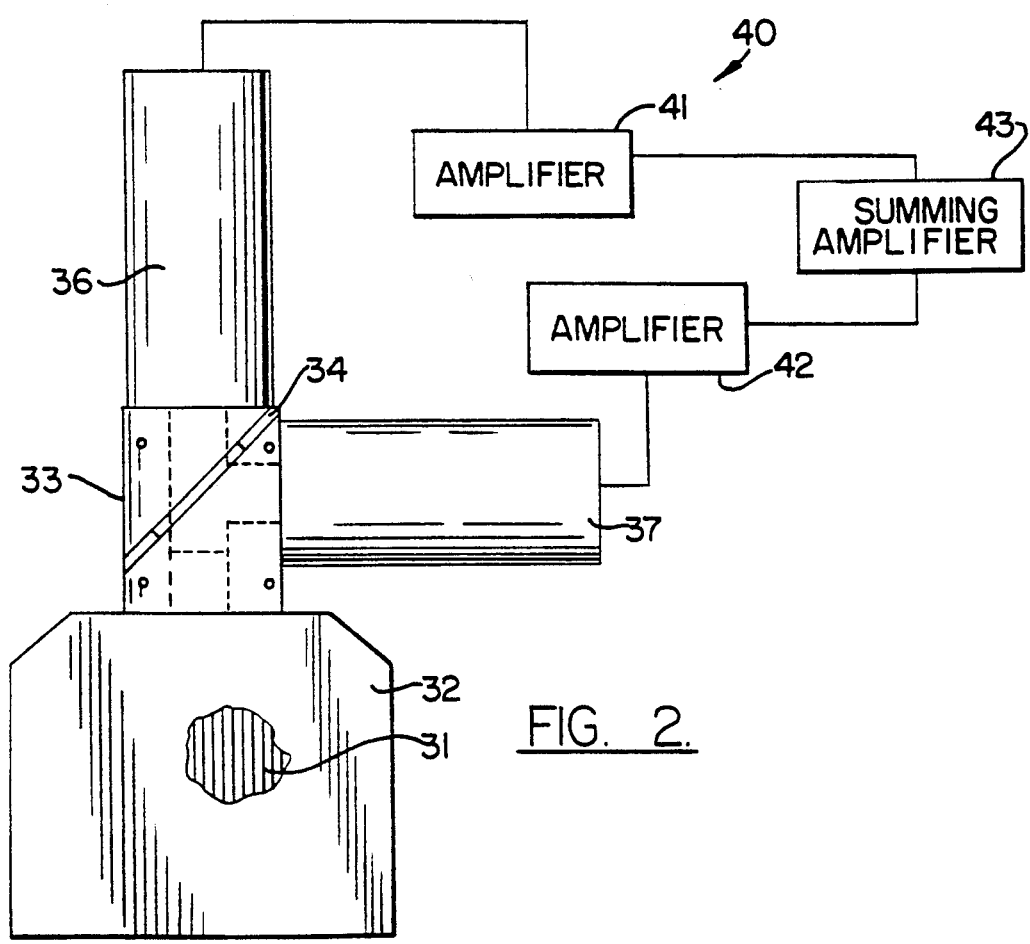
FIG. 2 is an enlarged schematic side view of the detector as illustrated in FIG. 1 and having a fiber optic bundle with parts broken away for clarity, a beam splitter, two photodetectors, and electrical circuitry according to the present invention.

FIG. 2 is an enlarged schematic view of the detector 30 for detecting particle defects from the scattered light forming the dark channel according to the present invention. This view also shows the fiber optic bundle 32 with parts broken away to illustrate the individual fibers 31, within the bundle 32. The fiber optic bundle 32 has the fibers 31 at a lower end arranged in a linear array so that light which is scattered along the scan line may enter the fibers At the upper end, the fibers are arranged in a group. Thus, the line of scattered light is brought into a concentrated spot.

The collar 33 is connected to and adjacent the upper end of the fiber optic bundle 32. The collar 33 houses the beam splitter 34 and has two open ends connected to two PMTs 36, 37. The beam splitter 34 is angularly positioned within the collar 33 to receive the collected spot of light from the fiber optic bundle 32. The beam splitter 34 divides or splits the light into two like components. The two PMTs 36, 37, and electrical circuitry broadly designated at 40 are positioned adjacent the collar 34 at substantially right angles therefrom so as to cooperate with the light beam splitter 34 and the fiber optic bundle 32 to thereby detect the particles or flaws on the surface of the wafer 11 as discussed above.

The PMTs 36, 37 electrically communicate with the electrical circuitry 40 of this embodiment. The electrical circuitry typically has amplifiers 41, 42, which electrically communicate with the PMTs 36, 37 for amplifying the output electrical signal from the respective PMTs 36, 37. A first and a second analog signals from the PMTs 36, 37 are amplified by the respective amplifiers 41, 42. A summing amplifier 43 electrically communicates with the amplifiers 41, 42 electrically communicating with the PMTs 36, 37 to combine the respective output signals from the PMTs 36, 37 and thereby produce a higher S/N than traditional systems. Alternately, the output signals from the photodetectors could be converted to digital signals and then combined in a summing amplifier or the like. It will be apparent to those skilled in the art that various techniques may be used for amplifying and combining the output signals from photodetectors, such as the PMTs 36, 37, used for detecting the light components. Further, it will also be apparent that various elements of the electrical circuitry, such as the amplifiers 41, 42 may be positioned within a portion of the PMTs 36, 37 for space, reliability, or other operational purposes.

Figure 3:
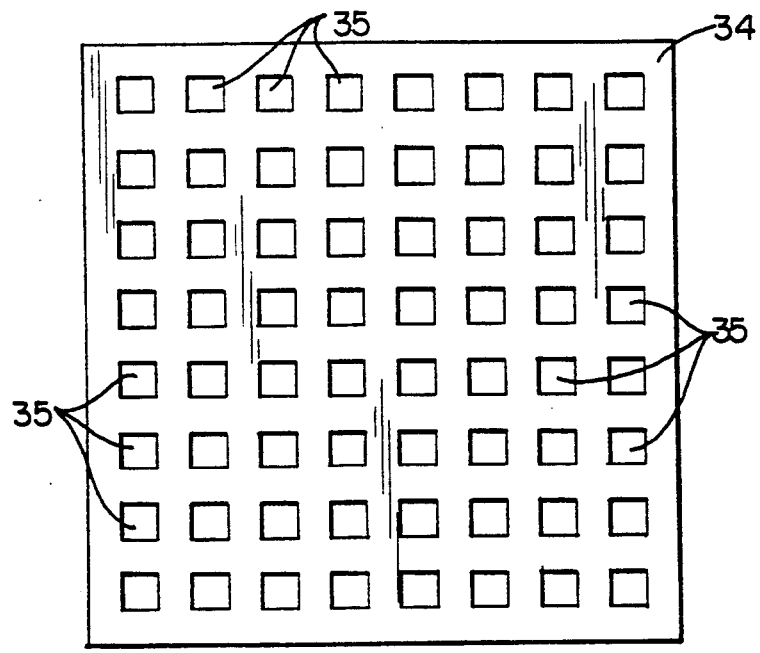
FIG. 3 is an enlarged plan view of a non-polarized beam splitter according to the present invention.

FIG. 3 is an enlarged plan view of the light beam splitter 34 for dividing the collected scattered light into first and second like light components as discussed in FIG. 2. In FIG. 3, according to a preferred embodiment, the light beam splitter 34 is non-polarized and has rectangular reflective segments 35 arranged as an optical element for evenly splitting the light received from the fiber optic bundle 32 into first and second like light components. These first and second like light components are then detected by the two photodetectors 36, 37 positioned to receive the light from the beam splitter 34. The rectangular reflective segments typically have a mirrored surface to reflect about half of the light received from the fiber optic bundle into the PMT 37 and the remaining portion of the surface of the beam splitter 34 is substantially transparent so as to allow about half of the light received from the fiber optic bundle 32 to be transmissively transmitted into the PMT 36. The rectangular reflective segments 35 are one embodiment for having half of the surface area of the light beam splitter 34 reflective and half of its surface area transmissive, but other techniques for dividing the light by use of a non-polarized beam splitter, such as an upper half of the surface being mirrored and a lower half being substantially transparent or reversing the transmissive and reflective orientation of the rectangular segments 35, will also be apparent to those well skilled in the art.

Figure 4:
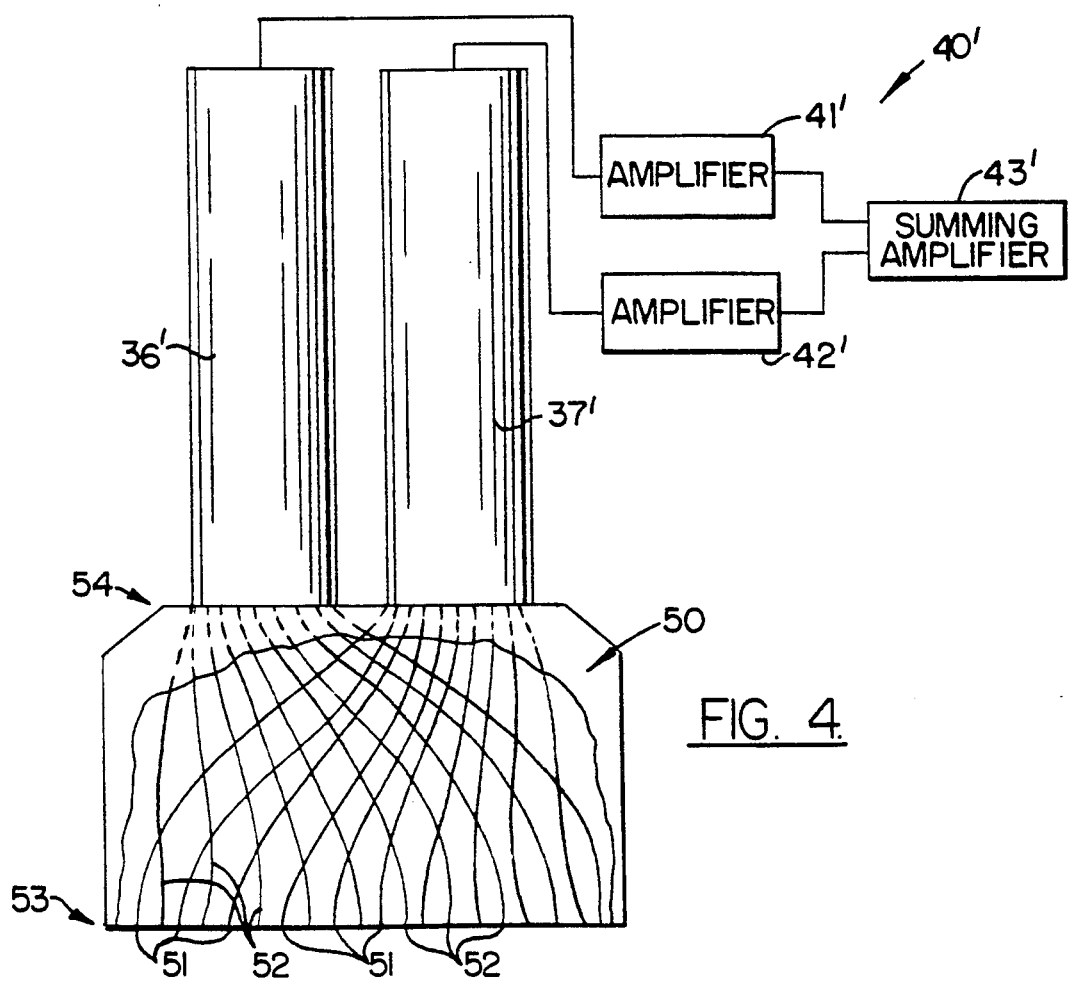
FIG. 4 is an enlarged schematic side view of an alternative embodiment of the detector according to the present invention having a dual output fiber optic bundle, two photodetectors positioned for receiving the output from the fiber optic bundle, and electrical circuitry.

Referring now to FIG. 4, illustrated is an alternative embodiment of the light collector for collecting the scattered light from an article, like elements are designated by use of prime (') notation. The light collector in this embodiment has a dual output fiber optic bundle 50 with separate outputs for separate strands of fibers designated generally at 52 passing through the fiber optic bundle 50. One end, designated generally at 53, of the fibers 51, 52 is arranged in a linear array to receive and collect the scattered light along the scan line. The other end, designated generally at 54, of the fibers 51, 52 is arranged in two groups to form the first and second like light components. PMTs 36', 37' are connected to the end 54 of the dual output fiber optic bundle 50 to receive the first and second like light components. The PMTs 36', 37' produce output electrical signals to be sent electrical circuitry 40' which electrically communicates with the PMTs 36', 37' The output signals are sent from the PMTs 36, 37 to amplifiers 41', 42' for amplification. The amplifiers 41', electrically communicate with summing amplifier whereby the amplified electrical signals are then sent to the summing amplifier 63 for combining the electrical signal outputs from the PMTs 36', 37' and increasing the S/N for the system 10. Although FIGS. 3 and 4 are illustrative of embodiments for dividing the scattered light received in the dark channel other techniques well known to those skilled in the art may also be used.

In the drawings and specification, there has been disclosed a typical preferred embodiment of the invention and, although specific terms are employed, they are used in a generic and descriptive sense only and not for the purposes of limitation, the scope of the invention being set forth in the following claims.

That which is claimed is:

1. A system for detecting particles or flaws on a surface of an article, comprising:
   a source of light directed against a surface of an article; and
   a detector for detecting light scattered from the article and indicative of the presence of particles or flaws thereon, said detector including a light collector positioned for receiving and collecting light scattered from the surface of the article , means cooperating with said collector for splitting a beam of the collected light into first and second like light components each representative of the beam of the collected light, first and second photodetectors positioned for receiving respectively the first and second like light components, and means for combining the output signals from said first and second photodetectors to form a combined output signal.

2. A system according to claim 1, wherein said source of light comprises a laser for producing a laser beam and laser scaling means or scanning the laser beam across the surface of the article.

3. A system according to claim 2, wherein said laser scanning means comprises a scanning mirror.

4. A system according of claim 1, wherein said photodetectors comprise photomultipliers.

5. A system according to claim 1, wherein said means for splitting the beam of the collected light comprises a non-polarizing light beam splitter.

6. A system according of claim 1, wherein said light collector comprises a fiber optic bundle.

7. A system according to claim 1, wherein said light collector and said means for splitting the collected light comprise a dual output fiber optic bundle.

8. A system according of claim 1, wherein said first and second photodetectors generate respective first and second analog output signals, and said means for combining the output signals from said first and second photodetectors comprises means for summing the first and second analog output signals.

9. A system for detecting particles or flaws on a surface of an article, comprising:
   laser scanning means positioned for scanning a laser beam along a scan line across a surface of an article; and
   a detector positioned for receiving laser light scattered of he surface of the article and indicative of the presence of particles or flaws thereon, said detector including a light collector for receiving and collecting the light which is scattered from the surface along the scan line, a light splitter mounted for receiving the light collected by said collector and for splitting a beam of the collected light into first and second like light components each representative of the beam of the collected light, first and second photodetectors cooperating with said light splitter for receiving respectively the first and second like light components, and means of combining the output signals from said first and second photodetectors.

10. A system according to claim 9, wherein said light splitter is a non-polarizing light splitting mirror having half of its surface area reflective and half of its surface area transmissive.

11. A system according to claim 9, wherein said collector means comprises a bundle of optical fibers, one end of the fibers being arranged in a linear array for receiving and collecting the scattered light along the scan line, the opposite end of the fibers being arranged in a group so as the concentrate the collected light into a light spot.

12. A system according to claim 9, wherein said collector means and said light splitter comprise a bundle of optical fibers, one end of the fibers being arranged in a linear array for receiving and collecting the scattered light along the scan line, the opposite end of the fibers being arranged in two groups to form said first and second like light components.

13. A system according to claim 9, wherein said first and second photodetectors generate respective first and second analog output signals, and said means for combining the output signals from said first and second photodetectors comprises means for summing the first and second analog output signals.

14. A system for detecting particles or flaws on a surface of an article, comprising:
   means for transporting an article along a predetermined path of travel past an inspection zone;
   means for scanning a laser beam along a predetermined path in the inspection zone for passing across a surface of the article;
   a fiber optic bundle positioned or receiving and collecting light scattered from the surface of the article;
   a light splitter cooperating with said fiber optic bundle for splitting a beam of he collected light into first and second like light components each representative of the beam of the collected light;
   first and second photodetectors positioned for receiving respectively the first and second like light components; and
   electrical means of combining the output signals from said first and second photodetectors to form a combined output signal.

15. A system according to claim 14, wherein said fiber optic bundle comprises a bundle of optical fibers, one end of the fibers being arranged in linear array for receiving and collecting the scattered light along the scan line, the opposite end of the fibers being arranged in a group to form a light output for the light received and collected therein.

16. A system according to claim 14, wherein said light splitter is a non-polarized light splitting mirror having half of its surface area reflective and half of its surface area transmissive.

17. A system according to claim 14, wherein said photodetectors comprise photomultipier tubes.

18. A system according to claim 14, wherein said electrical means comprises first and second amplifiers for amplifying the output signal from said first and second photodetectors and a summing amplifier for combining the amplified output signals from said first and second amplifiers.

19. A system for detecting particles or flaws on a surface of an article, comprising:
   means for transporting an article along a predetermined path of travel past an inspection zone;
   means for scanning a laser beam along a predetermined path in the inspection zone for passing across a surface of the article;
   a dual output fiber optic bundle positioned for receiving and collecting light scattered from the airspace of the article and splitting a beam of the collected light into first and second like light components each representative of the beam of the collected light;
   first and second photodetectors positioned for receiving respectively the first and second like light components; and
   electrical means for combining the output signals from said first and second photodetectors to form a combined output signal.

20. A system according to claim 19, wherein said dual output fiber optic bundle comprises a bundle of optical fibers, one end of the fibers being arranged in a linear array for receiving and collecting the scattered light along the scan line, the opposite end of the fibers being arranged in two groups to form said first and second like light components.

21. A system according to claim 19, wherein said photodetectors comprise photomultiplier tubes.

22. A system according to claim 19, wherein said electrical means comprises first and second amplifiers for amplifying the output signal from said first and second photodetectors and a summing amplifier for combining the amplified output signals from said first and second amplifiers.

23. A method for detecting particles or flaws on a surface of an article comprising the steps of:
   directing light onto a surface of an article;
   collecting light scattered from the surface of the article;
   splitting a beam of the thus collected scattered light into first and second like light components;
   optically detecting the first and second like light components to produce first and second detected output signals; and
   combining the first and second detected output signals to form a composite signal which is indicative of particles or flaws on the surface of the article.

24. A method according to claim 23, wherein said step of directing light onto the surface of the article comprises scanning a laser beam along a scan line across a surface of the article; and
   wherein said step of collecting the light scattered from the surface of the article comprises collecting the light scattered along the scan line.

25. A method according to claim 23, further comprising the step of electrically processing the combined output signals so as to indicate the presence of particles or flaws on the surface of the article.

* * * * *

UNITED STATES PATENT AND TRADEMARK OFFICE
CERTIFICATE OF CORRECTION

PATENT NO. : 5,329,351

DATED : July 12, 1994

INVENTOR(S) : Lee D. Clementi

It is certified that error appears in the above-identified patent and that said Letters Patent is hereby corrected as shown below:

Column 1, line 49, delete the word -- disk -- .

Column 4, line 9, delete "A first and a" and insert -- First and second --.

Column 4, line 38, after "segments" add -- 35 --.

Column 4, line 40, after "bundle" insert -- 32 --.

Column 4, line 60, after "at" insert -- 51, --.

Column 5, line 2, after "sent" insert -- to --.

Column 5, line 5, after "41'," add -- 42' --.

Column 6, line 47, after the words beam of "he" should be -- the -- .

UNITED STATES PATENT AND TRADEMARK OFFICE
CERTIFICATE OF CORRECTION

PATENT NO. : 5,329,351
DATED : July 12, 1994
INVENTOR(S) : Lee D. Clementi

It is certified that error appears in the above-identified patent and that said Letters Patent is hereby corrected as shown below:

Column 5, line 6, between "amplifier" and "whereby", insert -- 43 --.

Column 5, line 40, "scaling" should be -- scanning --.

Column 5, line 66, delete the words "of he" and insert -- from the --.

Signed and Sealed this

Twenty-seventh Day of September, 1994

Attest:

BRUCE LEHMAN

*Attesting Officer*  *Commissioner of Patents and Trademarks*